United States Patent
Jacob et al.

(10) Patent No.: US 10,299,744 B2
(45) Date of Patent: May 28, 2019

(54) SCINTILLATOR SEALING FOR SOLID STATE X-RAY DETECTOR

(71) Applicants: General Electric Company, Schenectady, NY (US); Teledyne DALSA, Inc., Waterloo, Ontario (CA); Teledyne DALSA B.V., Eindhoven (NL)

(72) Inventors: Biju Jacob, Niskayuna, NY (US); Brian David Yanoff, Niskayuna, NY (US); William Andrew Hennessy, Schenectady, NY (US); Jeffery Jon Shaw, Ballston Lake, NY (US); Douglas Albagli, Clifton Park, NY (US); Bartholomeus G. M. H. Dillen, Eindhoven (NL); Inge Peters, Eindhoven (NL); Anton Van Arendonk, Irricana (CA)

(73) Assignees: GENERAL ELECTRIC COMPANY, Schenectady, NY (US); TELEDYNE DIGITAL IMAGING, INC., Waterloo (CA); TELEDYNE DALSA B.V., Eindoven (NL)

( * ) Notice: Subject to any disclaimer, the term of this patent is extended or adjusted under 35 U.S.C. 154(b) by 204 days.

(21) Appl. No.: 15/354,760

(22) Filed: Nov. 17, 2016

(65) Prior Publication Data

US 2018/0132804 A1 May 17, 2018

(51) Int. Cl.
*A61B 6/00* (2006.01)
*H01L 27/146* (2006.01)
(Continued)

(52) U.S. Cl.
CPC .......... *A61B 6/4208* (2013.01); *G01T 1/2018* (2013.01); *G01T 7/00* (2013.01); *H01L 27/14634* (2013.01); *H01L 27/14663* (2013.01)

(58) Field of Classification Search
CPC ......... G01T 1/2018; G01T 1/24; G01T 1/244; G01T 7/00
See application file for complete search history.

(56) References Cited

U.S. PATENT DOCUMENTS 3,055,101 A 9/1962 Bergan
5,274,237 A 12/1993 Gallagher et al.
(Continued)

FOREIGN PATENT DOCUMENTS

JP 2012-47627 A 3/2012
WO 2008147135 A1 12/2008

OTHER PUBLICATIONS

Extended European Search Report and Opinion issued in connection with corresponding EP Application No. 17199890.9 dated Apr. 12, 2018.
(Continued)

*Primary Examiner* — Dani Fox

(57) ABSTRACT

An x-ray detector comprises: a housing, including a cover removably fastened on a flange of a flanged base and forming a semi-hermetic seal therebetween, the flanged base including a bottom surface and the flange surrounding a perimeter of the bottom surface; and an x-ray imager positioned on the bottom surface, the x-ray imager including a scintillator and an image sensor, wherein the seal semi-hermetically encloses the x-ray imager in the housing, and is positioned nonadjacently to surfaces in contact with the x-ray imager. In this way, a simpler and less costly seal for a digital x-ray panel can be provide; furthermore, the seal is
(Continued)

reusable and resealable, facilitating repair and refurbishment of the device.

19 Claims, 10 Drawing Sheets

(51) Int. Cl.
*G01T 1/20* (2006.01)
*G01T 7/00* (2006.01)

(56) References Cited

U.S. PATENT DOCUMENTS

| | | | |
|---|---|---|---|
| 5,641,984 A | 6/1997 | Aftergut et al. | |
| 6,642,524 B2 | 11/2003 | Vafi et al. | |
| 6,927,379 B2 | 8/2005 | Hoffman | |
| 7,126,130 B2 | 10/2006 | Hennessy et al. | |
| 7,473,903 B2 | 1/2009 | DeJule et al. | |
| 8,415,628 B1 | 4/2013 | Shaw et al. | |
| 2007/0007460 A1 | 1/2007 | Hochstetler et al. | |
| 2007/0114429 A1 | 5/2007 | Bhadare | |
| 2014/0211921 A1 | 7/2014 | Bandis | |
| 2014/0252229 A1 | 9/2014 | Kondo | |
| 2015/0008330 A1 | 1/2015 | MacLaughlin et al. | |
| 2015/0293237 A1 | 10/2015 | Suzuki et al. | |

OTHER PUBLICATIONS

"Home: PAVE Technology," PAVE Technology Website, Available Online at http://www.pavetechnologyco.com/html/home.html, Available as Early as Dec. 8, 2004, Retrieved Nov. 18, 2016, 2 pages.
"PAVE-Flex® Flat Cable Hermetic Seals Product Listing Index," PAVE Technology Website, Available Online at http://www.pavetechnologyco.com/design/flex_productindex.html, Available as Early as Oct. 13, 2005, Retrieved Nov. 18, 2016, 2 pages.
Jacob, B. et al., "Radiation Detector Assembly," U.S. Appl. No. 14/985,739, filed Dec. 31, 2015, 30 pages.
Jacob, B. et al., "Radiation Detector Assembly," U.S. Appl. No. 14/985,785, filed Dec. 31, 2015, 31 pages.
Jacob, B. et al., "Scintillator Sealing for Solid State X-Ray Detector," U.S. Appl. No. 15/354,820, filed Nov. 17, 2016, 47 pages.
Konkle, N. et al., "Scintillator Sealing for Solid State X-Ray Detector," U.S. Appl. No. 15/358,352, filed Nov. 22, 2016, 44 pages.

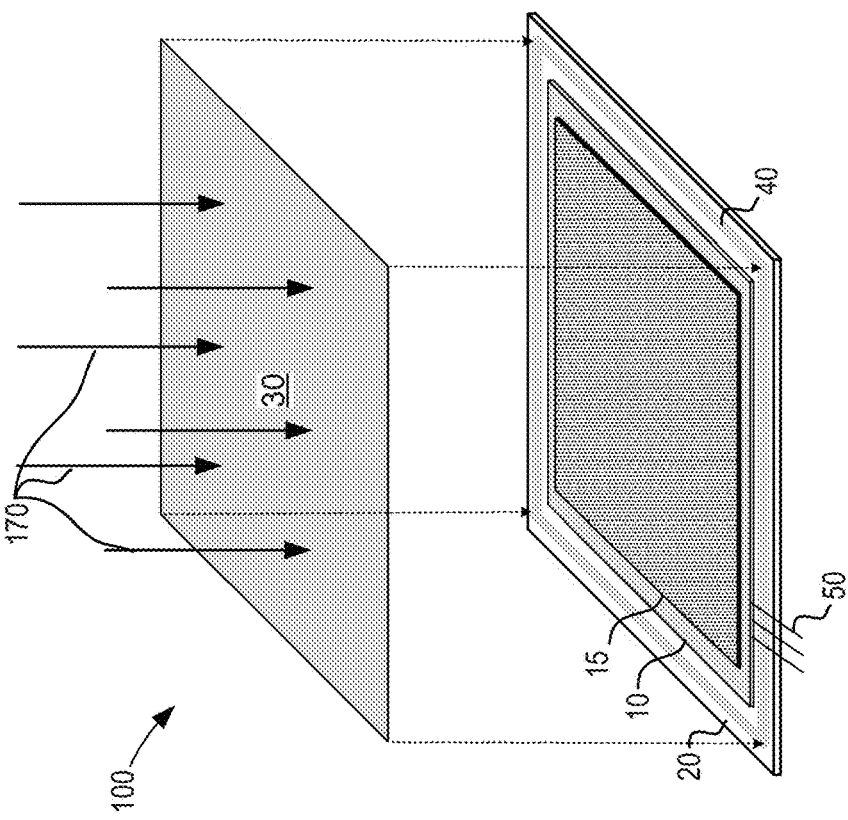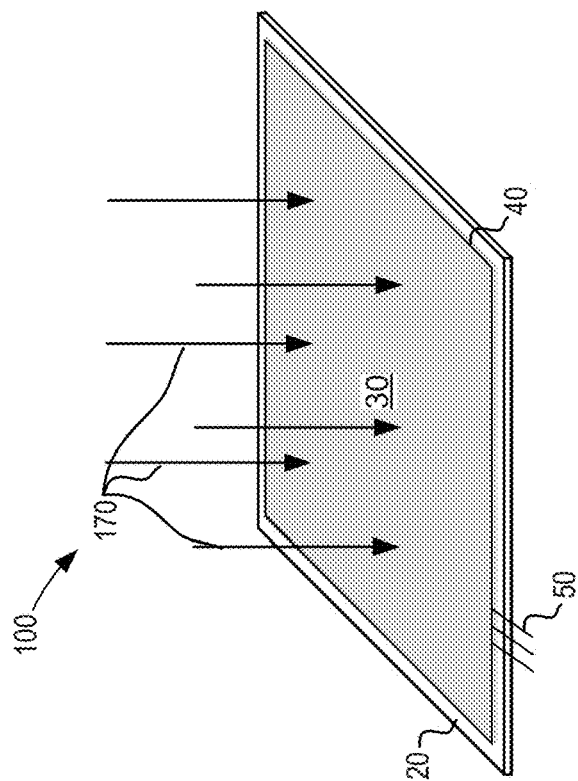

SCINTILLATOR SEALING FOR SOLID STATE X-RAY DETECTOR

FIELD

Embodiments of the subject matter disclosed herein relate to a solid state x-ray detector. Other embodiments relate to a solid state x-ray detector system and methods of assembling an x-ray detector.

BACKGROUND

X-ray detectors are used in medical diagnostic imaging, medical therapy, and various medical testing and material analysis industries. A common type of x-ray detector uses scintillator materials to convert x-ray photons into visible-spectrum photons as part of the energy detection process, and solid state electronics to convert the visible light photons into digital signals. Scintillator materials can have an affinity to absorb moisture, and solid state electronics may corrode in the presence of moisture, both of which can adversely affect the structure of the scintillator and degrade the image quality of the image detector.

In one embodiment Dejule et al. (U.S. Pat. No. 7,473,903) describe a digital x-ray panel including an x-ray detector formed on a detector substrate, a dam formed on the detector substrate circumscribing the detector matrix, a scintillator material formed on the detector matrix, and a hermetic layer formed on the scintillator material extending on to the surface of the dam. The hermetic layer is deposited as a thin film or coating in an active detector area over the scintillator and detector matrix, encapsulating and hermetically sealing them therein. In other embodiments, additional hermetic seals are provided at a chest wall side of the digital x-ray panel comprising bonding adhesive sealant between an edge of the hermetic layer and a sidewall, and bonding adhesive sealant between an edge of the hermetic layer and an end channel. In another embodiment, an additional hermetic seal is provided comprising bonding adhesive sealant to seal a gap between a protective cover and the hermetic layer.

The inventors herein have recognized various issues with the above approach. Namely, forming a hermetic seal as a coating or thin film on the scintillator requires film deposition equipment which can increase manufacturing time and costs. Furthermore, because of its proximity to the active layers of the x-ray detector, forming the hermetic seal coating or thin film can damage the scintillator, detector matrix, or solid state electronics of the digital x-ray panel. Further still, forming a seal over the active detector area can interfere with the performance of the digital x-ray panel since incident x-rays must be transmitted through the seal prior to reaching the scintillator. Further still, providing multiple hermetic seals within an x-ray detector increases manufacturing complexity and costs. Further still, hermetic seals formed with thin film coatings and bonded adhesive sealant are not removable and resealable, rendering repair and refurbishing of the x-ray panel more difficult and costly.

BRIEF DESCRIPTION

In one embodiment, the issues described above may be at least partially addressed by an x-ray detector, comprising: a housing, including a cover removably fastened on a flange of a flanged base and forming a seal therebetween, the flanged base including a bottom surface and the flange surrounding a perimeter of the bottom surface; and an x-ray imager positioned on the bottom surface, the x-ray imager including a scintillator and an image sensor, wherein the seal semi-hermetically encloses the x-ray imager in the housing, and is positioned nonadjacently to surfaces in contact with the x-ray imager.

In another embodiment, an x-ray imaging system comprises: a power source; a housing, including a cover removably fastened on a raised flange of a flanged base thereby forming a resealable seal therebetween; and an x-ray imager, including a scintillator and an image sensor, the x-ray imager positioned on a bottom surface of the flanged base inside the housing below and nonadjacent to the resealable seal, the raised flange surrounding a perimeter of the bottom surface; and an electrical connector conductively coupled to the x-ray imager and the power source.

In another embodiment, a method of assembling an x-ray detector including an x-ray imager, a housing, and an electrical connector conductively coupled to the x-ray imager, comprises: positioning the x-ray imager on a bottom surface of the housing, the housing comprising a cover and a raised flange surrounding a perimeter of the bottom surface, and the x-ray imager comprising a scintillator and an image sensor; and sealing the x-ray imager within the housing, including removably affixing the cover on a top surface of the raised flange to form a resealable seal between the cover and the raised flange, wherein the resealable seal is positioned outside of a path of x-rays incident at the x-ray imager.

In this way, the technical effect of providing a seal for a digital x-ray panel in a simple, low cost way can be achieved. Further technical effects are listed as follows. In the case where the seal is reusable and resealable, the technical effect of facilitating repair and refurbishment of the device is provided. Further still, the seal is positioned away from the detector-active region and thus does not interfere with the detector operation, and reduces a risk of damaging the detector components during manufacturing. Further still, positioning the seal away from the detector-active region can facilitate addition of other components within the x-ray detector housing such as getter material, sensors, electrical connectors, and the like, which can increase the performance and functionality of the x-ray detector. Further still, the seal facilitates sealing multiply-tiled large image array detectors within a single x-ray detector. Further still, the resealable seal may comprise a semi-hermetic resealable seal or a hermetic resealable seal.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 1A and 1B are schematics showing perspective views of an x-ray detector with a seal bonded at the detector substrate surface.

DETAILED DESCRIPTION

The following description relates to various embodiments of an x-ray detector, an x-ray detector system, and a method for assembling an x-ray detector.

In one embodiment, the issues described above may be at least partially addressed by an x-ray detector, comprising: a housing, including a cover removably fastened on a flange of a flanged base and forming a seal therebetween, the flanged base including a bottom surface and the flange surrounding a perimeter of the bottom surface; and an x-ray imager positioned on the bottom surface, the x-ray imager including a scintillator and an image sensor, wherein the seal may semi-hermetically enclose the x-ray imager in the housing, and may be positioned nonadjacently to surfaces in contact with the x-ray imager.

X-ray detectors use scintillator materials to convert x-ray photons into visible-spectrum photons as part of the energy detection process. The detector is sealed to prevent moisture from being absorbed into the scintillator, as moisture can adversely affect the crystal structure of the scintillator materials and degrade the image quality of the image detector. The solid state electronics, which convert the visible-spectrum photons to electrical signals in the image detector should also be protected from moisture to prevent their corrosion and consequent performance degradation. Current methods used to hermetically seal x-ray detectors include using an epoxy sealant to bond a cover to the top layer of the image detector or the image detector substrate, as shown in FIG. 1. Bonding the cover to the image detector to hermetically seal the x-ray detector can increase a risk of damaging the image detector due to the proximity of the seal to the image detector components; also, a non-resealable seal such as an epoxy bond can render repairs unworkable and costly since breaking the seal can damage the detector.

Figure 2B:
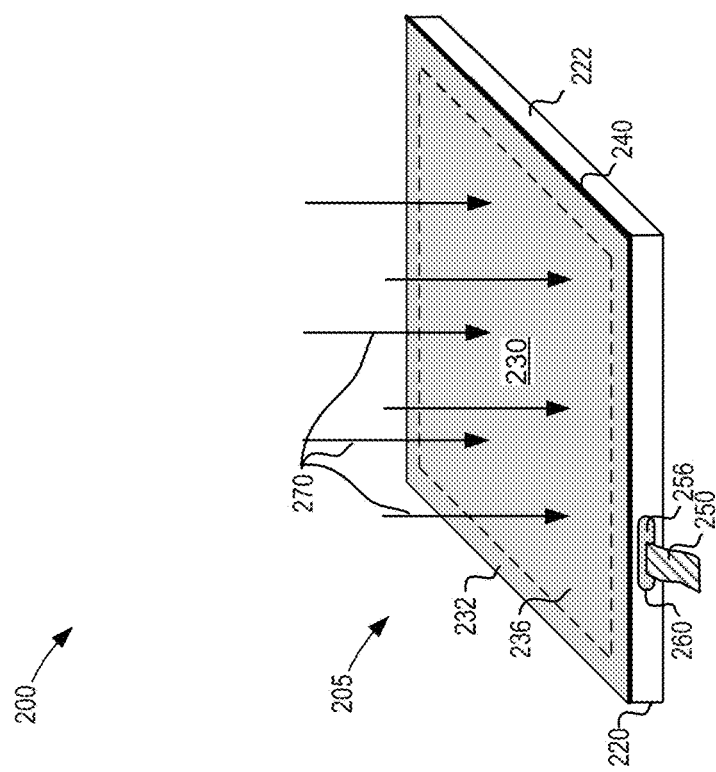
FIGS. 2A and 2B are schematics showing perspective views of an x-ray detector including a resealable seal.
Figure 2A:
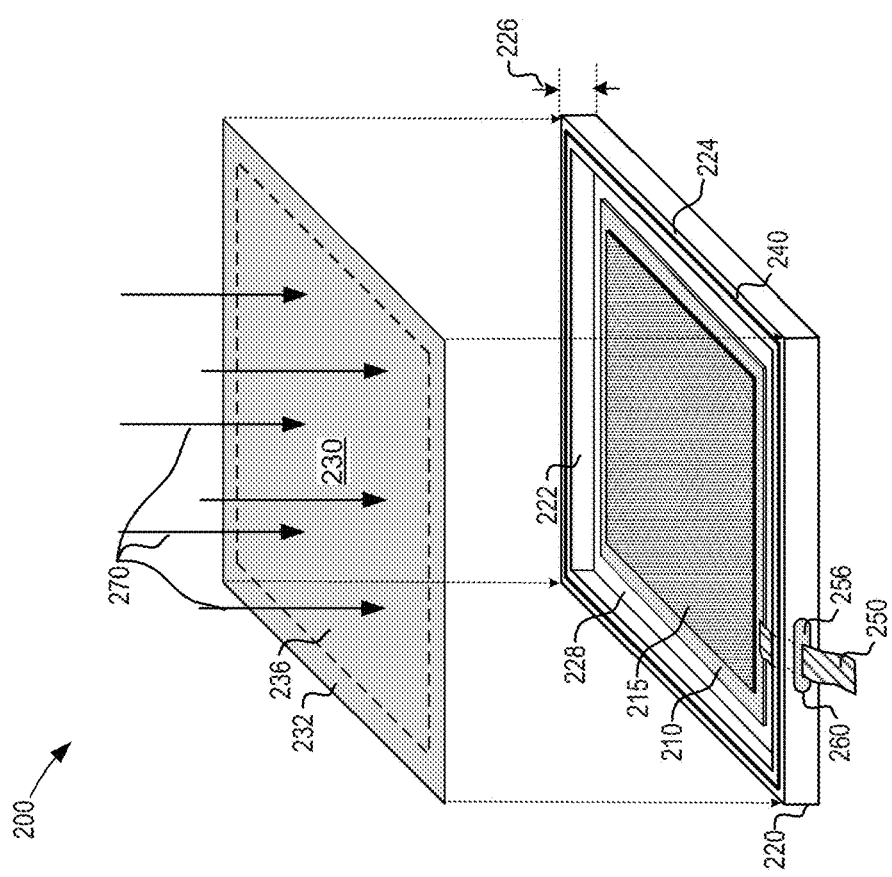
Figure 3:
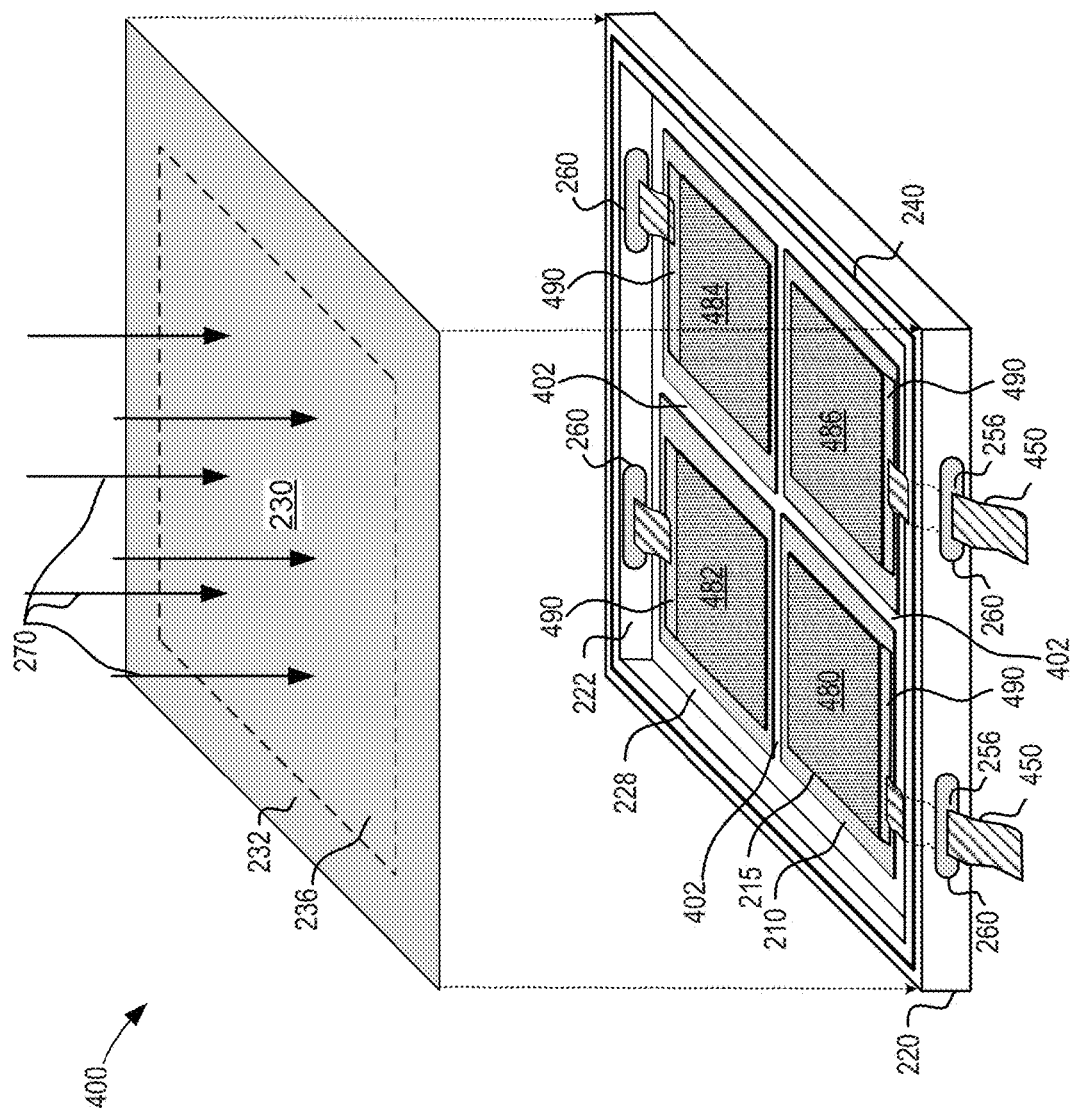
FIG. 3 are schematics showing a perspective view of an x-ray detector including tiled x-ray imagers and a resealable seal.
Figure 4C:
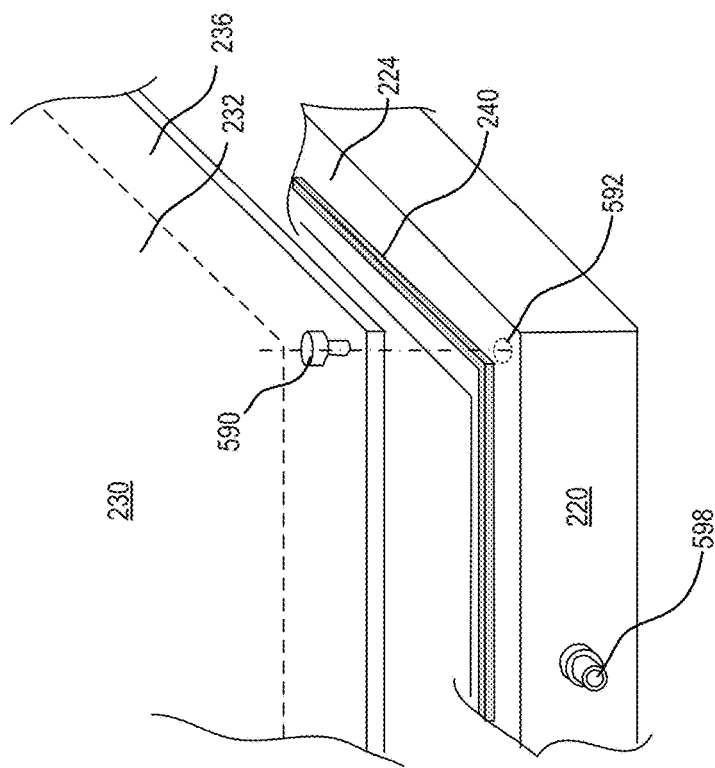
FIGS. 4A-4C are schematics showing enlarged partial perspective views of x-ray detectors including a resealable seal.
Figure 7:
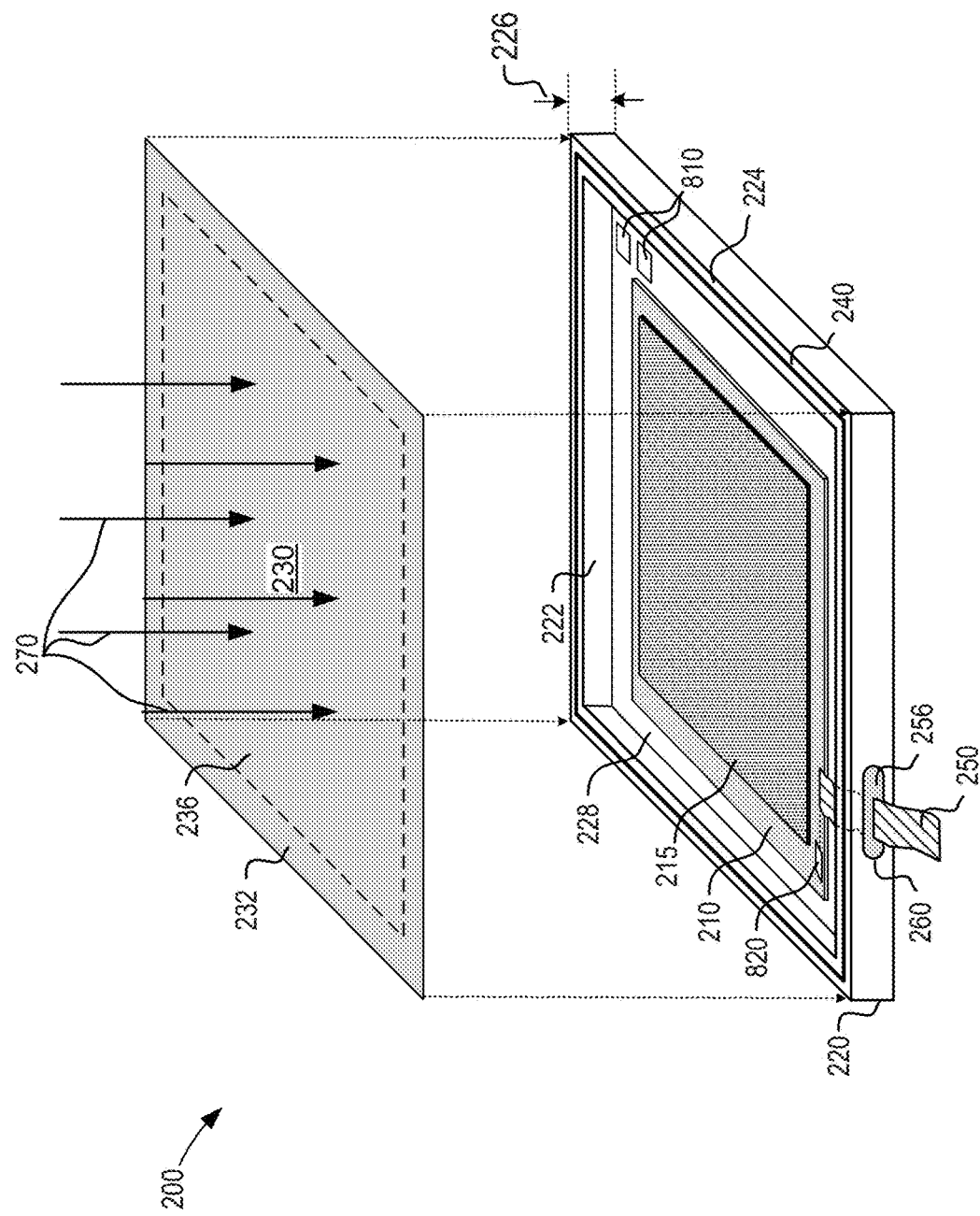
FIG. 7 is a schematic showing an expanded perspective view of an x-ray detector including a resealable seal.
Figure 8:
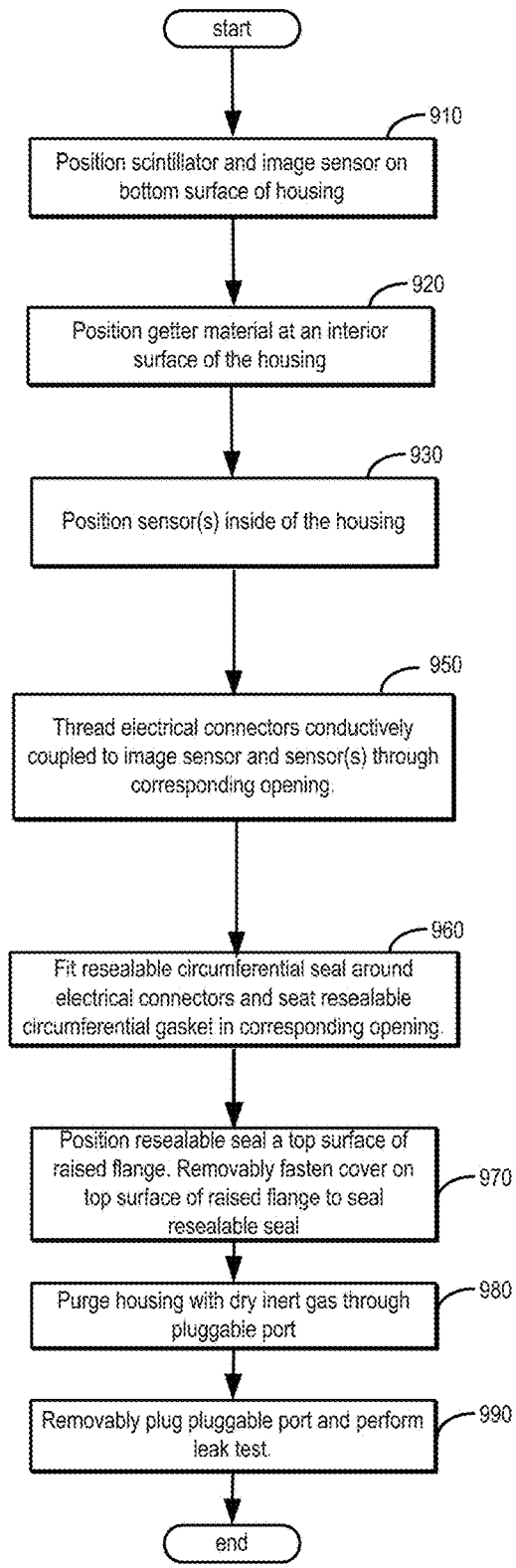
FIG. 8 is an example flow chart for a method of assembling the x-ray detectors of FIGS. 2A, 2B, 3, 4A-4C, and 7.

Accordingly, an improved x-ray detector including a resealable seal is shown in FIGS. 2A and 2B. In some embodiments, the resealable seal may be used for sealing large image array x-ray detectors configured with multiply-tiled Complementary Metal Oxide Semiconductor (CMOS) detectors, as shown in FIG. 3. The resealable seal can be configured in various ways as shown by FIGS. 4A-4C, 6A-6C, and FIG. 10. As shown in FIG. 5, long-term performance of the resealable seal is beyond the target and matches the baseline performance of current non-resealable (e.g., bonded) hermetic seals. The x-ray detector configuration with the resealable seal also facilitates addition of getter material, sensors, and other components (as shown in FIG. 7) within the x-ray detector that can increase detector performance and/or life. The resealable seal also aids in simplifying x-ray detector assembly methods, and x-ray resealing methods, as shown in FIG. 8.

Turning now to FIGS. 1A and 1B, they illustrate a schematic of a flat panel x-ray detector 100 having a non-resealable bonded adhesive seal 40. FIG. 1A illustrates a partially exploded view of the x-ray detector 100 with its cover 30 raised above the x-ray imager, the x-ray imager comprising the scintillator 15 and the image detector 10 layers. Incident x-rays 170 are directed through the cover 30 of the x-ray detector 100 where they are absorbed by the scintillator layer 15 and converted to visible light photons. Some examples of scintillator materials include ionic salts such as cesium iodide (CsI), a hygroscopic, crystalline material, with needle-shaped crystals. CsI crystals are oriented perpendicular to the plane of an adjacent (e.g., glass) substrate 20 and act as short optical fibers to ensure that visible light photons originating in a crystal preferentially exit the crystal at its end and into an adjacent corresponding photodetector, rather than propagating among adjacent crystals within the CsI layer. The visible light photons exiting the scintillator material are sensed by the image detector 10, which converts and outputs them as digital signals from the detector via connectors 50. The output digital signals are then input into a computer processor, where they are processed into an image for display.

Current methods used to seal x-ray detectors vary depending on the type of image sensor. In an amorphous silicon-based imager as shown in FIG. 1, the scintillator (CsI) is usually grown on the glass thin film transistor (TFT) panel. The x-ray detector housing cover 30 is bonded to the glass detector substrate 20 with an epoxy seal 40, providing a semi-hermetic barrier at each edge of the cover 30, as shown in FIG. 1B. In a CMOS (Complementary Metal Oxide Semiconductor) based image sensor the scintillator is usually grown on a different substrate (e.g., fiber optic plate) and the seal is achieved by coating the exposed area with organic materials that provide moisture barrier like parylene. Organic materials, such as epoxy adhesives, sealants, and coatings, do not provide hermeticity, but rather offer a low diffusion rate of moisture, the diffusion rate being dependent upon the morphology of the seal, the path length required for moisture to penetrate through diffusion, and the quality of their adhesion to the surfaces they are sealing. In some cases, epoxy or other organic adhesive sealants are provided in addition to the coatings to augment the seal path length, thereby increasing the moisture diffusion time through the seal. Epoxy sealants, adhesives, and organic coatings are thus semi-hermetic seals.

Both the epoxy seal and the coating seal approaches are non-resealable seals that are formed directly on the x-ray detector scintillator, image detector, and/or substrate layers in contact therewith. Forming a non-resealable seal as a coating or thin film on the scintillator requires film deposition equipment which can increase manufacturing time and costs. Furthermore, because of its proximity to the active layers of the x-ray detector, forming the seal, coating, or thin film can damage the scintillator, detector matrix, or solid state electronics of the digital x-ray panel. Further still, forming a seal over the active detector area can interfere with the performance of the digital x-ray panel since incident x-rays 170 must be transmitted through the seal prior to reaching the scintillator. Further still, providing multiple seals within an x-ray detector increases manufacturing complexity and costs. Further still, seals formed as thin film coatings or bonded adhesive are not removable and resealable, rendering repair and refurbishing of the x-ray panel more difficult and costly.

The evolution of digital x-ray detectors has included the development of CMOS (Complementary Metal Oxide Semiconductor) based digital x-ray detectors. Digital CMOS x-ray detectors are drawing more attention and becoming more popular in the area of fluoroscopic x-ray imaging especially in surgical and interventional applications because they exhibit extremely low electronic noise. These solid state electronic components should also be protected from moisture to prevent their corrosion and consequent performance degradation. CMOS imagers further comprise large active image areas required for radiography applications are realized by tiling multiple sensors into a larger sensor panel. Large-pixel tile array CMOS detector technology is well-suited for use in radiological-imaging applications because it is manufacturable in large areas, meets or surpasses radiological performance requirements, and offers digital-imaging system design flexibility not available from other radiological-imaging technologies. However, these large tile array imagers are more challenging for conventional semi-hermetic scintillator seals, such as adhesive and coating sealants formed on the surfaces of the tiled components and substrates, because the surface topology of a multi tile-array is much more complex than that for a single tile. For example, tiled imagers have seams between the tiles and water can find its way into the seams. Furthermore, tiled imagers do not have a continuous substrate surface on which a seal can be applied to a cover, rendering it more difficult for coating and thin film type seals to prevent moisture intrusion and degradation of the tiles.

Reference will be made below to exemplary embodiments of the inventive subject matter, examples of which are illustrated in the accompanying drawings. Wherever possible, the same reference numerals used throughout the drawings refer to the same or like parts.

Turning now to FIGS. 2A and 2B, they illustrate an embodiment of an x-ray detector 200, including a resealable seal 240 for sealing a scintillator 215 and an image sensor 210 inside a housing. The housing comprises a cover 230 and a flanged bathtub-structured base with a bottom surface 228 and a raised flange 220 surrounding the perimeter of the bottom surface 228. In FIGS. 2A and 2B, the bathtub housing is rectangular in geometry, however in other embodiments, the shape of the bathtub housing can take on other geometries such as circular, triangular, polygonal, non-symmetrical shapes, and the like. The cover comprises a central, active region 236 (delineated by the dashed border) through which x-rays 270 are incident into the x-ray detector 200, and a sealing region 232 around the perimeter of the cover 230 where x-rays 270 are non-incident. Accordingly, the sealing region 232 may form a picture frame layout surrounding the active region 236 of the cover 230. Dimensions of active region 236 may correspond to the dimensions of the scintillator 215 and/or image sensor 210 so that essentially all incident x-rays 270 are directed through the cover 230 to the scintillator 215 and image sensor 210. In some examples, the sealing region 232 of the cover may be constructed to be thicker in dimension to provide greater structural strength and rigidity for sealing and attaching the cover to the raised flange 220, while the active region 236 may be constructed to be thinner in dimension to reduce a risk of interference with the incident x-rays 270 to the x-ray detector 200. Similar to the sealing region 232 of the cover 230, the raised flange 220 may comprise a rigid solid material to provide greater structural strength and rigidity for sealing and attaching the cover 230 to the raised flange 220.

The housing may be made from many different types of solids including aluminum, stainless steel, other metals, polymers, combinations thereof, and the like. In one example, the housing may be constructed of a magnesium alloy, to yield a lighter-weight structure. In another example, the housing may be constructed from a carbon fiber composite coated or laminated with a metal coating or sheet to provide increased hermeticity at and in the vicinity of the surfaces of the sealing region 232 and the raised flange 220. The central active region 236 may be constructed from aluminum, although a fiber reinforced composite material having a thin metal coating or sheet covering may also be utilized. The flanged base may be constructed as one continuous piece of the solid material or as several pieces joined together using an attachment that hermetically seals the pieces together.

Each side of the raised flange 220 extends upward from the bottom surface 228 creating a cavity volume for positioning the x-ray detector components such as the scintillator 215 and the image sensor 210. In the non-limiting example depicted in FIGS. 2A and 2B, the housing is generally rectangular having sides that are approximately 90 degrees from the bottom and having a pair of matching parallel sides. In other embodiments the housing may comprise a non-rectangular shape and the walls of the raised flange could extend upward from the bottom surface 228 at a non-perpendicular angle. It should be understood that a person of ordinary skill in the art would understand that the compartment is not limited in its shape or geometry. The resealable seal 240 may be designed to match the shape and geometry and dimension of the sealing surfaces (e.g., the top surface 224 and the sealing region 232) so that a continuous seal can be formed surrounding the perimeter of the raised flange 220. In this sealing design, the resealable seal 240 along with sealing surfaces (e.g., the top surface 224 and the sealing region 232) can all be easily scaled in size and in shape. Furthermore, the housing bottom surface may be the same dimensions as the image sensor 210, or it may be of a larger dimension on one or more sides, leaving portions of the perimeter of the bottom surface 228 uncovered by the image sensor 210, as shown in FIG. 2A. Having portions of the perimeter of the bottom surface 228 uncovered by the image sensor 210 may be helpful for spacing and positioning additional components such as getter material or sensors, and the like, as further discussed hereinafter. Increasing spacing and reducing crowding of components within the housing can aid in reduction of heat accumulation within the housing, thereby reducing a risk of degradation of the x-ray detector.

The housing cover 230 may be shaped to match the dimension and perimeter of the raised flange 220. In some embodiments, the cover 230 may extend slightly beyond the perimeter of the raised flange 220, defining an overlapping lip that can aid in sealing the x-ray detector 200, as discussed hereinafter. The cover 230 may be constructed from a rigid, solid material designed to create a semi-hermetic seal when attached to the raised flange 220, as shown in FIG. 2B. The cover 230 can be a thin sheet of aluminum, another low atomic number metal, a composite structure with laminated metal foils, other metals, a plastic, or any other hermetic material. The cover may be homogeneous in thickness or may vary in thickness to ease manufacture. In some embodiments, the cover 230 may comprise a thinner central active region 236 and a thicker perimeter sealing region 232, as shown in FIG. 2. The thinner central active region 236 may be constructed from a low atomic number (e.g., low density) metal such as aluminum so to reduce any interference with incident x-rays 270 into the x-ray detector. The thicker sealing region 232 may be constructed from a strong, rigid material for maintaining the structural integrity of the cover and for maintaining integrity of the sealing surface contacting the resealable seal 240.

The resealable seal 240 may comprise a compressible, homogeneous, sealable material such as a rubberized, polymeric, metallic, or non-metallic gasket. Metallic gaskets may provide for a hermetic resealable seal. A non-metallic gasket may provide a semi-hermetic seal, but may advantageously impart a higher resealability to the resealable seal 240. As a further example, the resealable seal 240 may comprise a composite structure including a non-metallic gasket coated or covered with a metallic coating or sheeting to provide both increased hermeticity and increased resealability. The resealable seal 240 may also comprise a resealable adhesive, however the resealability may depend on the resealability of the adhesive; for example, resealability may decrease due to partial reductions in adhesiveness when the seal is resealed. Furthermore, the resealable seal 240 comprises a continuous member that surrounds the perimeter of the bottom surface 228. As such, when the cover 230 is attached to the raised flange 220, as shown in FIG. 2B, the resealable seal 240 is compressed and sandwiched between sealing region 232 and the top surface 224, thereby sealing the x-ray detector 200. The seal provided by the resealable seal 240 may be a hermetic seal or a semi-hermetic seal, the type of seal depending at least partially on the nature of the material of construction of the resealable seal 240. The sealing region 232 and the top surface 224 along with the resealable seal 240 thus form the sealing surfaces for the x-ray detector. As described above, example materials that can be used for the resealable seal 240 include metallic, non-metallic, and both metallic and non-metallic materials. For example, the resealable seal 240 may be constructed of a metal or a glass, or other ceramic or semiconductor material. A resealable seal 240 constructed of metal or glass may provide a seal having increased hermeticity relative to non-metallic and non-glass seal materials. Some examples of non-metallic resealable seal materials include nitrile rubber, Neoprene, Viton, butyl rubber, and ethylene propylene diene monomer (EPDM) rubber.

The resealable seal 240 may be homogeneous in that it is constructed of a single homogeneous body of material throughout. In other embodiments, the resealable seal 240 may be homogeneous in that it is constructed with a uniform and continuous cross-section throughout. In some examples, the cross-section of the resealable seal 240 may comprise a solid cross-section of material, and in other examples, the resealable seal 240 may comprise a hollow cross-section of material and the hollow cavity within the resealable seal 240 may be evacuated or filled with an inert dry gas. In this way the integrity of the resealable seal 240 may be increased and a risk of moisture intrusion into the x-ray detector is reduced (because there are no breaks or discontinuities in the seal body), as compared to conventional x-ray detector seals comprising a combination of both coatings or thin film layers and epoxy or other bonded seals.

The resealability of the resealable seal 240 may be imparted at least partially by its compressibility. Upon sandwiching the resealable seal 240 between the top surface 224 of the raised flange 220 and the sealing region 232 of the cover 230, the resealable seal 240 is essentially elastically (e.g., reversibly) compressed or deformed, thereby providing a seal therebetween. Thus, when the cover 230 is raised from the top surface 224 of the raised flange 220, the resealable seal 240 rebounds elastically back to its original form, shape, and volume. In this way, the components of the x-ray detector 200 may be serviced, and the resealable seal 240 may be resealed repeatedly by sandwiching the resealable seal 240 between the top surface 224 of the raised flange 220 and the sealing region 232 of the cover 230.

The resealability of the resealable seal 240 is also imparted at least partially because of the surface characteristics of the resealable seal 240. The outer surface of the resealable seal is smooth and continuous enough such that when compressed against the surfaces of the top surface 224 and the sealing region 232 of the cover 230, the region between the resealable seal 240 and those surfaces are sealed continuously with no gaps or discontinuities. In this way, if the surfaces of both the top surface 224 and the sealing region 232 are relatively flat, smooth and rigid, the sealing of the x-ray detector 200 is achieved more easily since the resealable seal can be more homogeneously compressed around the entire perimeter of the raised flange 220. Furthermore, the coefficient of friction between the surface of the resealable seal 240 and the top surface 224 and sealing region 232 should be high enough so that the resealable seal 240 does not slip off either surface when compressed therebetween. In some embodiments, a track or raceway for friction fit-seating the resealable seal 240 at the top surface 224 or the sealing region 232 may be provided to facilitate holding the resealable seal 240 between the top surface 224 and the sealing region 232 during the sealing process.

The resealability of the resealable seal 240 is also imparted at least partially because the resealable seal 240 is held in place non-permanently by friction and/or pressure when the resealable seal is sandwiched between the top surface 224 of the raised flange 220 and the sealing region 232 of the cover 230. As such, the resealable seal 240 is neither bonded nor permanently affixed to any surfaces of the x-ray detector 200, which facilitates removal and unsealing of the resealable seal 240 when the housing of the x-ray detector is opened. Furthermore, because the resealable seal 240 is neither bonded nor permanently affixed to the x-ray detector 200, resealing the resealable seal 240 precludes destroying (or irreversibly altering) and removing the original seal material and reapplying new sealing material in order to reseal the x-ray detector 200, as would be performed in the case of resealing a conventional bonded adhesive sealant or coating type of seal.

The scintillator 215 is positioned on the image sensor 210, and the image sensor 210 is positioned on the bottom surface 228 of the flanged base. As described above with reference to FIG. 1, the scintillator 215 absorbs incident x-rays 270 and converts them to visible light photons. Some examples of scintillator materials include ionic salts such as cesium iodide (CsI), a hygroscopic, crystalline material, with needle-shaped crystals. CsI crystals are oriented perpendicular to the plane of the bottom surface 228 substrate, and act as short optical fibers to ensure that visible light photons originating in a crystal preferentially exit the crystal at its end and into an adjacent corresponding photodetector, rather than propagating among adjacent crystals within the CsI layer. In some embodiments, the scintillator may also include thin layer coatings thereon which may be provided for corrosion protection, encapsulation, reflecting visible light, as a resistive mask during manufacturing, and the like. In all embodiments, the resealable seal 240 is positioned separate and apart from the x-ray imager (e.g., the scintillator and the image sensor). In addition, the resealable seal 240 is positioned separate and apart from any surfaces in contact with the x-ray imager, including any thin layer coatings deposited on the scintillator 215. Accordingly, the sealing region and sealing surfaces of the x-ray detector 200 is moved away from the x-ray detector components, which can reduce manufacturing defects and increase useful life of the x-ray detector.

Furthermore, positioning the resealable seal 240 on the top surface 224 and facilitates sealing x-ray detectors comprising a scintillator that is not formed on a glass substrate. Conventional method of manufacturing x-ray detectors permanently seal the x-ray detector cover to the glass substrate of the scintillator; next, electrical and data access connectors are etched into the glass. By moving the sealing region to between the top surface 224 of the raised flange 220 and the sealing region 232 of the cover 230, the electrical and data communication connectors 250 can be provided via a flex cable conductively coupled to the x-ray imager, and the electrical connectors 250 can be threaded through one or more openings 260 in the housing.

The visible light photons exiting the scintillator 215 are sensed by the image sensor 210, which converts and outputs them as digital signals externally from the x-ray detector 200 via electrical connectors 250. The image sensor 210 may comprise one or several pixels. Each pixel has a light photon sensitive area (e.g. a photodiode) that senses visible spectrum photons entering from the scintillator 215. The pixels convert the visible light, based on presence, absence, and intensity into a computer readable digital signal. The output digital signals are then input into a computer processor, where they are processed into an image for display.

To access these data a high speed digital interface connection is provided, with an electrical connector 250 that is conductively coupled to the image sensor 210 (or a printed circuit board, PCB, in electrical communication with the image sensor 210). In addition to transmitting digital signals externally from the x-ray detector, electrical connector 250 transmits the input signals that control and power the image sensor 210, scintillator 215, and other components housed inside the housing. In one embodiment, the electrical connector 250 can comprise a flexible ribbon cable, comprised of a combination of various individual connectors. The flexible quality, and flat aspect ratio of the electrical connector 250 aids in sealing around the electrical connector 250 as it is passed through the housing, as described below. However, the electrical connector 250 is not limited to flat cable ribbons, and other types of electrical connectors 250 can also be used and sealed using the systems and methods described herein. In the embodiment shown in FIGS. 2A and 2B, a single electrical connector 250 is conductively coupled to the image sensor 210; in other embodiments, multiple electrical connectors 250 may be conductively coupled to the image sensor 210 and passed through one or more sealed openings 260 in the housing. As shown in FIG. 2A, the electrical connector 250 is conductively coupled to the image sensor 210 at a position in the housing near the opening 260 and is threaded directly to the opening 260. In other examples, the location of the opening 260 and the location where the electrical connector 250 is coupled to the image sensor 210 may be farther away from each other than as shown in FIG. 2A, and a portion of the electrical connector 250 may be bundled or coiled adjacent to the inside walls of the raised flange 220 or along an exposed portion of bottom surface 228, so as to avoid interfering with incident x-rays 270 passing through the active region 236 to the scintillator 215.

In one embodiment, the electrical connector 250 may be passed or threaded through an opening 260 in the housing, thereby enabling electrical communication into and out from the housing. As shown in FIG. 2A, the opening 260 may be positioned at the side of the raised flange 220, however in other embodiments, the opening 260 may be positioned elsewhere in the housing, such as in bottom surface 228, or in the cover 230. Positioning the opening 260 in the bottom surface 228 or the raised flange 220 may be advantageous as compared to positioning the opening 260 in the cover 230 so as not to interfere with incident x-rays 270 in the active region 236 of the cover 230. Sealing of opening 260 around the electrical connector 250 can be established by a resealable circumferential seal 256 surrounding a transverse cross-section of the cable. In one embodiment, the circumferential seal 256 can be achieved by a rubberized polymeric, metallic, non-metallic, or combination thereof, gasket surrounding a transverse perimeter of the electrical connector 250. In some examples, the resealable circumferential seal 256 can be bonded to the electrical connector 250, while in other examples, the resealable circumferential seal 256 can be tightly friction fit around the electrical connector 250. In either case, upon compression of the resealable circumferential seal 256, a resealable seal between the resealable circumferential seal 256 and the electrical connector 250 is provided. The hermeticity (semi-hermetic or hermetic) of the seal may be determined by the hermeticity of the material of construction used for the electrical connector 250 and the resealable circumferential seal 256, however both semi-hermetic and hermetic resealable seals can be achieved.

An outer dimension of the resealable circumferential seal 256 may correspond in shape and dimension to the shape and dimension of opening 260. In other examples, the outer dimension of the resealable circumferential seal 256 may be slightly larger in shape and dimension to the shape and dimension of opening 260 so that when the resealable circumferential seal 256 is positioned at or inside the opening 260, the resealable circumferential seal 256 is elastically compressed, thereby providing at least a semi-hermetic resealable seal between the walls of the opening 260 and the resealable circumferential seal 256, and between the resealable circumferential seal 256 and the electrical connector 250. Similar to resealable seal 240, the resealable circumferential seal 256 reverts to its original dimension and elasticity when it is removed from the opening 260. In this way, the resealable circumferential seal 256 is imparted with a resealable quality since the electrical connector 250 and the resealable circumferential seal 256 can be disassembled from the opening 260 without destroying or irreversibly altering the resealable circumferential seal 256. Similar to the resealable seal 240 as described above, the resealability of the resealable circumferential seal 256 may be at least partially imparted by its compressibility, its surface characteristics, its homogeneity in its material of construction, and because it is held in place by friction and/or pressure (and not permanently bonded to a surface of the housing). In further examples, as described below with reference to FIG. 4B, the resealable circumferential seal 256 may comprise a single-lipped or double-lipped groove around its circumference, a thickness of the groove corresponding to a thickness of the opening 260. In this way, the resealable circumferential seal 256 and the sealing thereof may be augmented by a single or double lip on either side of opening 260.

The resealable seal 240 is positioned on the top surface 224 of the raised flange 220 and also surrounds the perimeter of the bottom surface 228, scintillator 215, and image sensor 210. A height 226 of the raised flange is greater than a combined thickness of the scintillator 215 and image sensor 210, and hence the top surface 224 of the raised flange and the resealable seal 240 are positioned at a horizontal plane above the plane of the scintillator 215. As such, the resealable seal 240 is positioned apart from the scintillator 215 and the image sensor 210, and separated from surfaces in direct contact with the scintillator 215 and the image sensor 210. In contrast with conventional coating or adhesive type x-ray detector seals, the resealable seal 240 is positioned at the enclosure boundary (e.g., raised flange 220) of the housing, instead of in proximity to the scintillator 215 and the image sensor 210 and the bottom surface 228 (detector substrate). Furthermore, by positioning the resealable seal 240 at the raised flange 220 of the housing, the resealable seal 240 is located outside of the path of the incident x-rays 270. As such, the resealable seal 240 does not interfere with or contaminate the x-ray detector imaging performance.

Turning now to FIG. 3, it illustrates an embodiment of an x-ray detector 400 comprising a multiply-tiled pixel array. In one example, x-ray detector 400 may include a CMOS x-ray detector having an image sensor panel comprising more than one pixel array. In the case of FIG. 3, the x-ray detector 400 includes an array of four pixel array tiles 480, 482, 484, and 486. Integrated with each of the pixel array tiles 480, 482, 484, and 486, are all the electronics in the CMOS sensor such as the electrical connectors 450, and the scintillator 215, so that incident x-rays 270 into each of the pixel array tiles are converted to visible light photons, where they are sensed and received by the image sensors 210, and the corresponding digital signals are transmitted out of the housing via electrical connectors 450. Each of the pixel array tiles connects to a wiring system that transmits the digital signals thereto and therefrom. As described above, the wiring system may include a printed circuit board ("PCB") 490 conductively coupled to the image sensor 210. The electrical connectors 450, shown in FIG. 3 as flexible ribbon cables, are used to connect and transmit signals from the pixel array tiles to a computer processor external to the housing (not shown). In the example of FIG. 3, the x-ray detector 400 includes four flexible ribbon cables (each corresponding to an individual pixel array tile) for transmitting the digital signals. In other examples, there may be more than one electrical connector 450 supporting communication to and from each pixel array tile. Furthermore, each electrical connector 450 is passed through one of four openings 260 in the housing. In other examples, as described above, multiple electrical connectors 450 may be passed through a single opening to reduce an amount of sealing and to reduce a risk of moisture intrusion into the x-ray detector 400. Sealing of the openings 260 in x-ray detector 400 may be achieved similarly as described above for x-ray detector 200, wherein a resealable circumferential seal 256 is attached around a transverse cross-section of each electrical connector 450 and seated in each of the openings 260. Similar to x-ray detector 200, a resealable seal 240 is compressed upon attaching cover 230 on raised flange 220, thereby sealing (semi-hermetically, or hermetically) the housing of x-ray detector 400.

Although the tiles of the pixel array are placed as close together as possible, abutting gaps 402 exist between the tiles. The abutting gaps 402 are vulnerable to trapping moisture that can degrade the scintillators 215 and the electronics inside the housing. Abutting gaps 402 are difficult to seal using conventional x-ray detector sealing methods such as thin films, coatings, and bonded sealants. By positioning the sealing surfaces of the x-ray detector 400 at the top surface 224 of the raised flange 220 and the sealing region 232 of the cover, away from and above the bottom surface 228 substrate and the surfaces in contact with the scintillators 215 and image sensors 210, the challenge of sealing the abutting gaps is averted, thereby simplifying and improving sealing of the x-ray detector 400 including multiply-tiled pixel array image sensor, as compared to conventional methods.

Figure 4A:
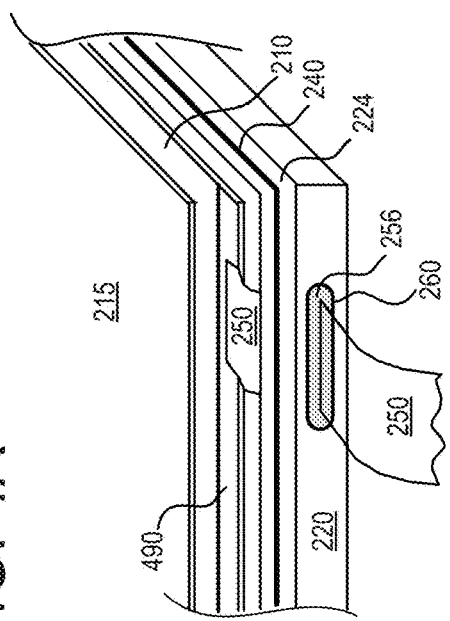
Figure 4B:
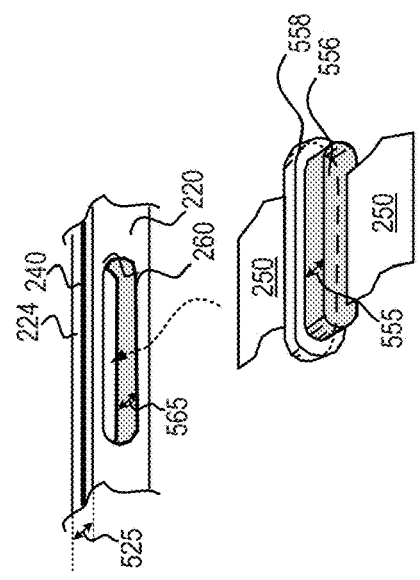
Figure 5:
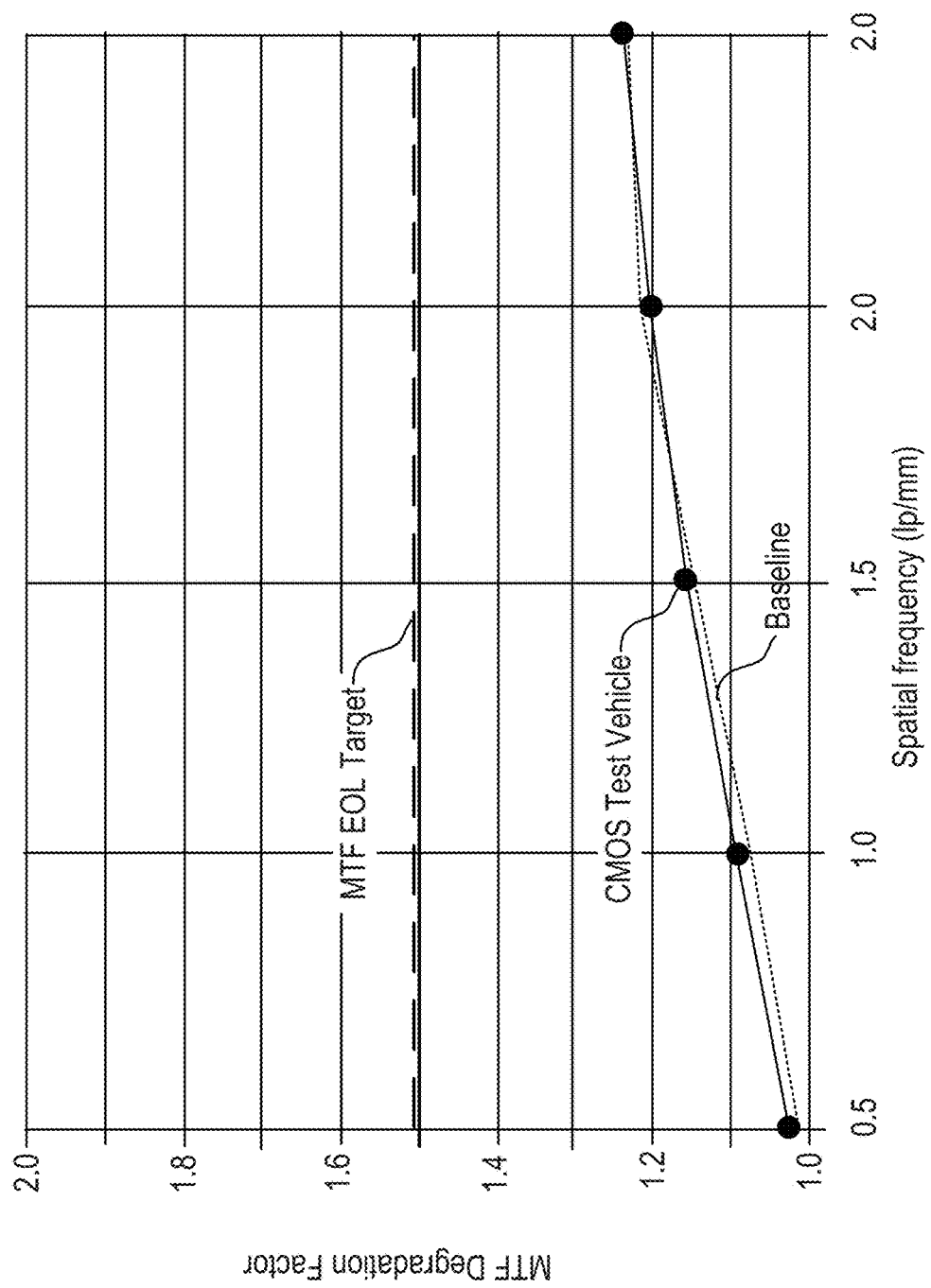
FIG. 5 is a plot illustrating performance of a resealable seal for the example x-ray detectors of FIGS. 2A, 2B, 3, 4A-4C, and 7.

Turning now to FIGS. 4A and 4B, they illustrate enlarged partial perspective views of a corner region of an x-ray detector 200 and a partially exploded perspective view of region surrounding an opening 260 in x-ray detector 200. As shown in FIG. 4A, electrical connector 250 is conductively coupled to PCB 490 of image sensor 210 at one end and is threaded through opening 260 in raised flange 220 to transmit and receive signals from and to the image sensor 210 positioned inside the x-ray detector housing. The opening 260 is shown as an ovular shaped opening through the wall of the raised flange 220, however, the shape of the opening 260 is not particularly limited. The geometry of opening 260 may be chosen to correspond to approximately the same geometry as a transverse cross section of the electrical connector 250, and the size of the opening 260 may be chosen to be somewhat smaller than the transverse cross section of the electrical connector 250, in order to be able to accommodate seating and sealing (compression) of the resealable circumferential seal 256 therein. In the example x-ray detector shown in FIG. 4A a single electrical connector 250 is threaded through the opening 260, however in other embodiments, particularly for x-ray detectors having multiply-tiled pixel arrayed image sensors, more than one electrical connector 250 may be threaded through the opening 260. In such a case, the geometry and dimension of the opening 260 may be adjusted accordingly to accommodate seating (and sealing) the plurality of electrical connectors 250 therein. In some cases the same sized resealable circumferential seal 256 may be used for multiple electrical connectors 250, and in such a case, the geometry and dimension of the opening may remain the same as for the case of sealing a single electrical connector 250 threaded therethrough. In other examples, multiple openings 260 in the housing may be provided for accommodating multiple electrical connectors 250, as needed. Reducing a number of openings 260 may aid in simplifying and increasing the seal integrity of the x-ray detector since fewer sealed openings are maintained, thereby reducing a risk of moisture intrusion.

As shown in FIG. 4B, the thickness 565 of the opening 260 may correspond to a thickness 525 of the raised flange 220 (e.g., the opening penetrates through the side of raised flange 220), and may further correspond to a thickness 555 of resealable circumferential seal 556. In this manner, upon seating and compressing the resealable circumferential seal 556 in the opening 260, a semi-hermetic or hermetic seal is formed across the entire thickness 565 of the raised flange 220. In this way, the hermeticity of the seal can be increased and the risk of moisture intrusion into the x-ray detector through the opening can be reduced. Also illustrated in FIG. 4B is an example of resealable circumferential seal 556 having a flanged side 558. The flanged side 558 is shown as a different shade in FIG. 4B for illustrative purposes, and can be formed along with the central portion of the circumferential resealable seal 556 as a single homogeneous and continuous seal. The flanged side 558 has a larger cross section than the central portion of the circumferential resealable seal 556. FIG. 4B shows the flanged side 558 as having the same shape as the central portion of the circumferential resealable seal 556, however the flanged side 558 may also have a geometry different therefrom. As stated earlier, the circumferential resealable seal 556 (and the flanged side 558) can be formed from rubberized, elastic, deformable material. Accordingly, when the circumferential resealable seal 556 including the flanged side 558 is deformed and compressed and the central portion of the circumferential resealable seal 556 is seated in the opening 260, the flanged side 558 aids in increasing a sealing contact surface area with the interior side wall of the raised flange.

In other examples, the circumferential resealable seal 556 may include two flanged sides 558 such that when the circumferential resealable seal 556 is seated in the opening 260, the flanged sides 558 provide additional sealed regions at both the interior and exterior walls of the housing around the areas of the opening 260 covered by the flanged sides 558. The flanged sides 558 may also facilitate seating of the circumferential resealable seal 556 by guiding and aligning the central portion of the circumferential resealable seal 556 to be seated along the entire thickness of the opening 260. The circumferential resealable seal 556 having one or two flanged sides 558 can be described as a grooved circumferential resealable seal 556, the central portion thereof forming a circumferential groove that is seated inside the opening 260.

Figure 10:
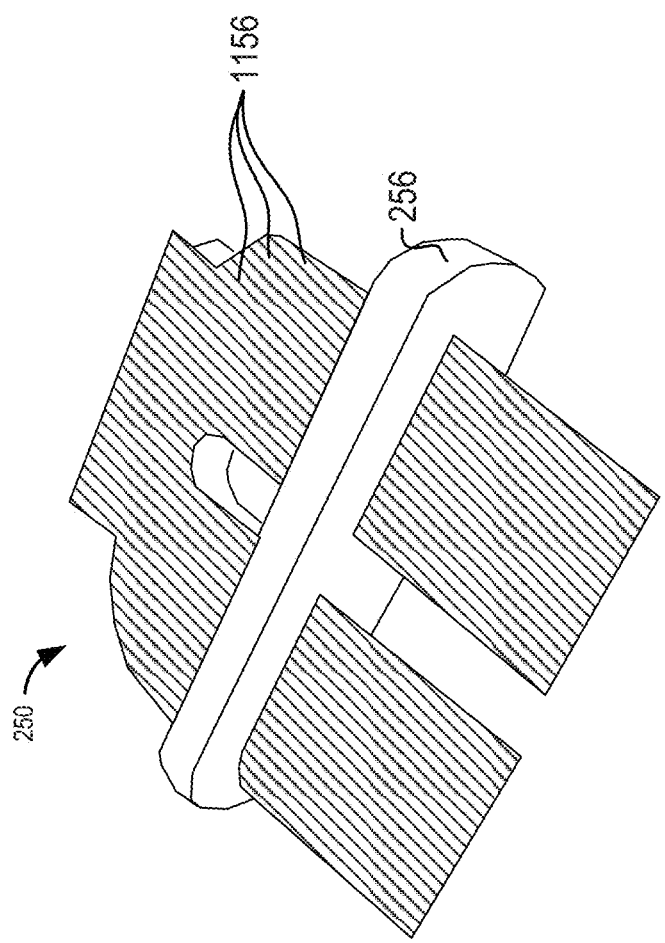
FIG. 10 is a schematic showing a perspective view of a resealable circumferential seal for an x-ray detector.

Turning now to FIG. 10, it illustrates a perspective view of another example of a flexible electrical connector 250 and a resealable circumferential seal 256. The electrical connector 250 may comprise an insulated, stranded or solid plated copper conductor in any combination or lengths, copper or brass connector pin contacts or glass fiber optic cables of any type. The electrical connectors 250 may comprise insulated solid conductor flat cables or high conductor density Kapton flex circuits. The resealable circumferential seal 256 may include compressible and flexible epoxy molded o-ring seals over the electrical connectors 250, and may include laser welded aluminum housings. As shown in FIG. 10, the resealable circumferential seal 256 may encompass one or more disparate arrays or sub-arrays of electrical connectors 250, each array comprising a flat ribbon cable including several individual wire connectors 1156. As previously described, the resealable circumferential seal 256 may be sized to be seated sealably in an opening 260 of the x-ray detector housing. The resealable circumferential seal 256 may be seated in the housing by fitting the resealable circumferential seal 256 around the electrical connector 250 and then screwing the seal into place to seat. Seating the resealable circumferential seal 256 in the opening 260 may further comprise friction fitting the resealable circumferential seal 256 into the opening 260, and compressing the resealable circumferential seal 256 in the opening 260.

Turning now to FIG. 4C, it illustrates an enlarged partially exploded perspective view of an x-ray detector 200. As shown in FIG. 4C, x-ray detector 200 may further comprise one or more fasteners 590 and one or more fastener receiving structures 592 located in the housing. The fasteners 590 may comprise a screw, bolt, nail, rivet, bracket, strap or other type of mechanical fastener that can be used for removably attaching the cover 230 to the raised flange 220. The fastener receiving structures 592 may comprise a hole, hook, or other structure designed to firmly attach cover 230 to the raised flange 220 when fastener 590 is received by fastener receiving structure 590. The fastener receiving structures 592 may be integrated into both the cover 230 and the raised flange 220, where needed. For example, threaded holes may be formed in the cover 230 and the top surface 224 of the raised flange 220 for receiving a screw, rivet, or bolt used for removably fastening cover 230 to the raised flange 220. The fasteners 590 and fastener receiving structures 592 may be evenly spaced around the perimeter of the cover sealing region 232 and the raised flange 220 so that upon fastening the cover 230 to the raised flange 220, the resealable seal 240 is adequately compressed around the entire perimeter of the sealing surfaces to (hermetically or semi-hermetically) seal the surfaces between the cover 230 and the raised flange 220. As described above the sealing region 232 may be thicker than the active region 236 of the cover 230 to impart increased structural rigidity to the cover 230 as it is fastened to the raised flange. Preserving rigidity of the cover 230 while fastening the cover 230 to the raised flange 220 can aid in evenly compressing the resealable seal 240 around the perimeter of the housing, which can reduce a risk of moisture intrusion into the x-ray detector 200.

The x-ray detector 200 may also comprise one or more additional pluggable ports 598. The pluggable port 598 can aid in detecting leaks in the housing assembly of the x-ray detector. In one example, the sealed x-ray detector 200 can be filled with dry helium gas via the pluggable port 598, after which the pluggable port 598 is plugged. Helium sensors can then be utilized to determine if any helium gas has leaked from any of the x-ray detector seals (e.g., resealable seal 240 and the sealed openings 260). The leak testing may also be conducted using other types of gases and gas sensors. Furthermore, the leak detection can also be performed by coating the outside of the seals with a liquid surfactant (e.g., dish soap and water, and the like).

Additionally, the interior of the sealed housing can be purged with dry nitrogen gas (or another dry inert gas) via the pluggable port 598 to displace any air (and moisture) therein. The pluggable port 598 may be sealed hermetically or semi-hermetically using an O-ring, gasket, epoxy, solder, rubber, polymer, or any sealing material now known or known in the future that will create a hermetic or semi-hermetic seal.

Turning now to FIG. 5, it illustrates a plot of modulation transfer function (MTF) degradation factor, a measure of the x-ray detector performance, versus spatial frequency. Data for FIG. 5 may be generated by submitting an x-ray detector to accelerated environmental testing in a high temperature high-humidity environmental chamber. The end-of-life (EOL) MTF target is plotted as the horizontal dashed line. MTF degradation factor performance of x-ray detectors comprising a resealable seal 240 sandwiched between the housing cover 30 and the raised flange 220 and a resealable circumferential seal 256 seated in the opening 260 through which the electrical connector 250 is threaded is comparable to baseline performance of conventional methods of sealing an x-ray detector (for example, as shown in FIGS. 1A and 1B). Accordingly, the method of assembling an x-ray detector described herein including providing a resealable seal 240 sandwiched between the housing cover 30 and the raised flange 220 and a resealable circumferential seal 256 seated in the opening 260 through which the electrical connector 250 is threaded, achieves the technical result of reducing moisture intrusion into the x-ray detector over its lifetime.

Turning now to FIGS. 6A-6D, they illustrate cross sectional views of several non-limiting example configurations of the resealable seal 240 sandwiched between the cover 230 and the raised flange 220. A dotted line delineates the thicker sealing region 232 from thinner active region 236 of the cover 230. As discussed earlier, the increased thickness of the sealing region 232 around the perimeter of the cover 230 increases structural rigidity of the cover when attaching the cover 230 to the raised flange 220, which can aid in increasing seal hermeticity since the resealable seal 240 is compressed more uniformly around the housing. Furthermore, reducing the thickness of the central active region 236 of the cover 230 can aid in increasing performance of the x-ray detector by reducing interference (e.g., absorption, deflection, and the like) with incident x-rays 270. Reducing the thickness of the active region 236 also reduces a weight of the x-ray detector, which can aid in improving the ergonomics and user-friendliness of the x-ray detector. The transition in thickness from the sealing region 232 to the active region 236 may be sharp, as shown for the example configurations of FIGS. 6A, 6B, and 6D, where the cover thickness abruptly changes at the boundary therebetween; alternately, as in the example configuration of FIG. 6C, the transition in thickness from the sealing region 232 to the active region 236 may be gradual, which can provide increased flexural strength to the cover, while reducing a weight of the cover.

Figure 6A:
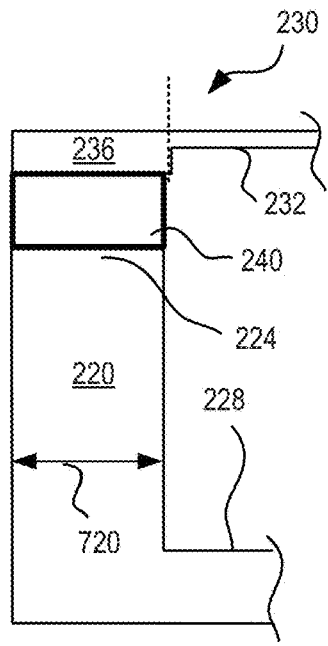
FIGS. 6A-6D are schematics showing enlarged cross-sectional views of resealable seal configurations used in the x-ray detectors of FIGS. 2A, 2B, 3, 4A-4C, and 7.

As shown in FIG. 6A, the resealable seal 240 may span a thickness 720 of the raised flange 220 and a thickness of the sealing region 232 of the top cover 230, and may be vertically sandwiched and compressed therebetween upon sealing the x-ray detector. The perimeter dimensions of the cover 230 match the perimeter dimensions of the raised flange 220, and hence when the cover is affixed to the raised flange 220, upon sealing the housing, an outer edge of the cover 230 is flush with the outer edge of the raised flange 220. A cross section of the resealable seal 240 is shown as rectangular, however, as described above, circular, ovular, hollow, or other cross-sectional geometries may be possible. An advantage of the rectangular cross-section shown is that both sealing surfaces of the resealable seal 240 fully span and contact the top surface 224 and the sealing region 232, which can enhance the hermeticity of the seal and reduce a risk of moisture intrusion into the x-ray detector. The thickness of the resealable seal 240 in alternate examples may be less than the thickness 720 of the raised flange 220, but can still achieve a semi-hermetic or hermetic seal upon compression of the resealable seal 240 between the cover 230 and the raised flange 220.

Figure 6B:
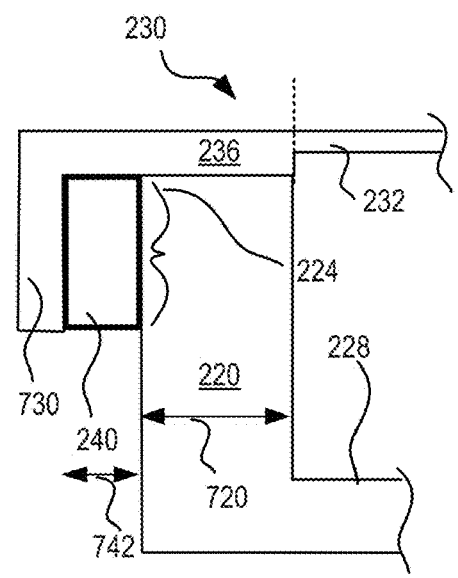

As shown in FIG. 6B, the cover 230 may overlap and overhang the outer edge of the raised flange 220, forming an overhanging lip 730. Accordingly, the resealable seal 240 may be sandwiched between the overhanging lip 730 of the sealing region 232 of the cover 230 and a top surface 224 of the raised flange 220. Here, the top surface 224 includes a top surface of the outer edge of the raised flange 220. The thickness of the resealable seal 240 may be formed slightly thicker than the thickness of the gap 742 formed between the overhanging lip 730 and the outer edge of the raised flange 220 so that when the cover 230 is attached to the raised flange 220, thereby horizontally compressing the resealable seal 240, the hermeticity of the seal is increased and a risk of moisture intrusion is reduced. The configuration of sandwiching the resealable seal 240 between the overhanging lip 730 and the outer edge of the raised flange 220 may be advantageous to increasing a hermeticity of the x-ray detector since the path length for moisture to diffuse through the seal is increased. For example, as shown in FIG. 6B, moisture must travel vertically upwards between the resealable seal 240 and the overhanging lip 730 or between the resealable seal 240 and the outer edge of the raised flange 220, and then across the thickness 720 of the raised flange 220 before reaching the interior of the housing.

Figure 6C:
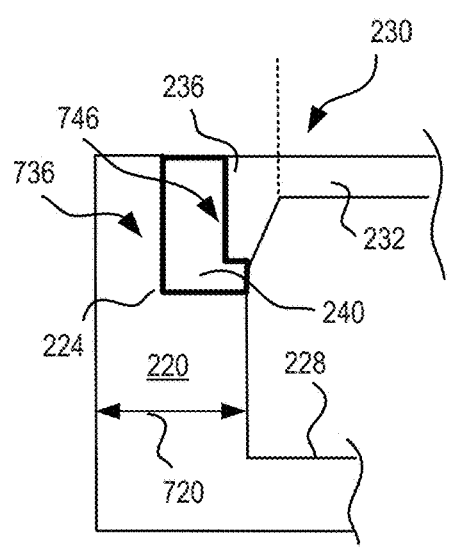

Turning now to FIG. 6C, it illustrates another example configuration of the resealable seal 240, raised flange 220, and cover 230. Raised flange may be shaped to include a cutout 736 into the top surface 224 of the raised flange 220 contacting and forming a sealing surface with the resealable seal 240. Similarly, the resealable seal 240 may also be formed to include a cutout 746 into the surface of the resealable seal 240 contacting and forming a sealing surface with the cover 230. Cutouts 736 and 746 serve to align and seat the resealable seal 240 on the raised flange 220 and the cover 230 on the resealable seal 240, respectively. In this way, the forming of the seal and the alignment of the opposing sealable surfaces between the resealable seal 240 and the raised flange 220, and between the cover 230 and the resealable seal 240, can be more reliably made each time the seal is resealed. Furthermore, the cutouts 736 and 746 also increase a distance and tortuosity that intruding moisture must travel in order to reach the housing interior, thereby increasing the seal hermeticity. As shown in FIG. 6C, the L-shaped cutouts 736 and 746 facilitate oblique (simultaneous horizontal and vertical) compression of the resealable seal when the cover 230 is fastened to the raised flange 220.

Figure 6D:
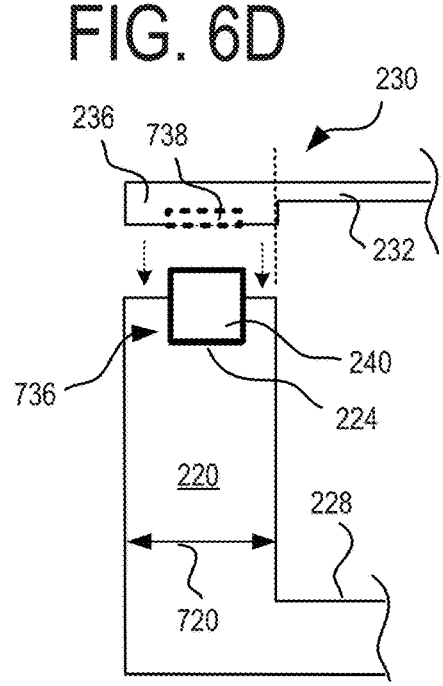

Turning now to FIG. 6D, it illustrates another example configuration of the resealable seal 240, raised flange 220, and cover 230. Here, the top surface 224 of the raised flange comprises a cutout 736 facing the resealable seal 240, and the cover 230 also includes a cutout 738 in the underside surface of the sealing region 232 facing the resealable seal 240. As shown in FIG. 6D, the cutouts 736 and 738 may be shaped to, in combination, correspond to a cross-sectional geometry of the resealable seal 240, and may be sized so that a combined cross-sectional area of the cutouts 736 and 738 may be slightly less than the cross-sectional area of the resealable seal 240. In this way, upon fastening the cover 230 to the raised flange 220, the resealable seal 240 may be compressed, thereby forming a seal therebetween with increased hermeticity. The cutouts 736 and 738 also increase a distance that intruding moisture must diffuse in order across the sealable surfaces (between the cover 230 and the resealable seal 240, and between the resealable seal 240 and the top surface 224 of the raised flange 220) to reach the interior of the housing. In FIG. 6D, the rectangular cross sectional geometries of the cutouts 736 and 738 and the resealable seal 240 are exemplary and non-limiting, and any practical cross-sectional geometry may be used, such has circular, ovular, regular polygonal, irregular polygonal, and the like.

Turning now to FIG. 7, it illustrates an additional embodiment of an x-ray detector 200, including additional components placed in the housing interior. Positioning the sealing region, including the resealable seal 240, the top surface 224 of the raised flange 220, and the sealing region 232 of the cover 230 apart and separated from the image sensor 210 and the scintillator 215 and the surfaces directly adjacent to and in contact therewith creates free volume within the housing in which additional components may be positioned. Because height 226 of the raised flange is greater than the height of the scintillator 215, image sensor 210, and bottom surface 228 combined, the sealing region is raised above a top surface of the scintillator 215 so that when the cover 230 is fastened to the top surface 224, there may be a space or gap between the top surface of the scintillator 215 and the undersurface of the cover 230. Furthermore, as shown in FIG. 7, the bottom surface 228 of the flanged base may be greater one or more dimensions than the scintillator 215 and the image sensor 210 such that there may exist a perimeter region of the bottom surface 228 where additional components may be placed in housing. For example, getter material 810 for absorbing moisture or other substances may be placed at an interior surface within the housing. The placement of the getter material may be concentrated at a particular location, as shown in FIG. 7 where the getter material 810 is placed in a corner of the bottom surface 228, or the getter material 810 may be distributed throughout interior surfaces of the housing. In one example, the getter material may be placed nearer to the sealing region, for example at the perimeter of the undersurface of the cover 230, or at the internal walls of the raised flange 220 near the interface with the fastened cover 230 to reduce a risk of moisture intrusion. In the case where the getter material is coated at the undersurface of the active region 236 of the cover, the getter material coating may be thin, of low density and non-absorptive towards the incident x-rays 270. As another example, the getter material 810 may be placed nearer to the opening 260 and the seated resealable circumferential seal 256 to reduce a risk of moisture intrusion. In another example, the getter material 810 may be placed nearer to the pluggable port 598 to reduce a risk of moisture intrusion. In another example, the getter material 810 may comprise a coating on one or more interior surfaces of the housing. As non-limiting examples, the getter material 810 may be coated at the underside of the cover 230, the interior walls of the raised flange 220, or along exposed areas of the bottom surface 228. The getter material 810 may further comprise sheets, strips, wires or sintered pellets of gas absorbing metals, or a paste applied to an interior housing surface. Moisture may preferentially be absorbed at the getter material 810 instead of the scintillator 215 or the image sensor (and other electronics components within the housing), thereby reducing a risk of x-ray detector degradation.

Furthermore, the getter material 810 may comprise an oxygen getter material to scavenge oxygen within the housing, for example, in the case of an x-ray panel detector comprising organic diodes. Oxygen getter material may comprise commercially available getter material from SAES group, Johnson Matthey, and the like. Further still, a shock absorption material can be used to protect the imager from damage inside the x-ray imager sealing housing. Shock absorption material comes in many forms including foam, solid, fibrous material and the like.

Various sensors 820 may also be positioned inside the x-ray detector housing, and may be conductively coupled to one or more of the image sensor 210, the scintillator 215, and the electrical connector 250. In one embodiment, sensors 820 may include a moisture or humidity sensor for detecting moisture intrusion into the housing. The moisture sensor 820 may transmit a digital signal to an x-ray detector controller positioned external to the housing, and the controller, may execute a responsive controlling action. For example, in response to a moisture level in the housing being greater than a threshold moisture level, the controller may generate an audio and/or visual alarm indication, and may reduce or shut off a power supply to the x-ray detector in order to reduce a risk of degradation to the x-ray detector. In another embodiment, sensors 820 may include a temperature sensor, and the controller, in response to a temperature being greater than a threshold temperature, may generate an audio and/or visual alarm indication, and may reduce or shut off a power supply to the x-ray detector in order to reduce a risk of degradation to the x-ray detector. As another example, sensors 820 may include an oxygen sensor to detect intrusion of air or oxygen into the housing, indicating seal integrity degradation. In response to an oxygen level being greater than a threshold oxygen level, the controller may generate an audio and/or visual alarm indication, and may reduce or shut off a power supply to the x-ray detector in order to reduce a risk of degradation to the x-ray detector.

Turning now to FIG. 8, it illustrates a method 900 for assembling an x-ray detector. Method 900 begins at 910 where the x-ray imager, comprising the scintillator 215 and the image sensor 210 are positioned on the bottom surface 228 of an x-ray detector housing. As described above, the x-ray detector may include a plurality of pixel array tiles, each tile in the pixel array comprising its own scintillator and image sensor and separated from other tiles by abutting gaps 402 therebetween (as shown in FIG. 3). Furthermore, the housing may comprise a flanged base, the perimeter of the bottom surface 228 being surrounded by a raised flange 220 whose height 226 is greater than the top surface of the x-ray imager. As such, the resealable seal 240 positioned the top surface 224 of the raised flange 220, is higher than the top surface of the x-ray imager. Further still, the dimensions of the bottom surface 228 may be greater than the dimensions of the x-ray imager so that there may be regions of the bottom surface 228 that are exposed and uncovered by the x-ray imager.

Next at 920, the getter material 810 may be positioned at an interior surface of the housing. The getter material may comprise a desiccant or other material that preferentially absorbs moisture (relative to the scintillator materials) and thus can aid in reducing a risk of degradation of the x-ray detector. The getter material may be coated on one or more interior surfaces of the housing, such as on the underside of the sealing region 232, the interior walls of the raised flange 220, or nearer to an opening 260 or pluggable port 598 in the housing. At 930, one or more sensors 820, such as a temperature and/or moisture sensor and/or oxygen sensor, may also be positioned inside the housing. The one or more sensors may be conductively coupled to the x-ray imager, and to an electrical connector 250 for transmitting the sensor output to a computer external to the housing.

Method 900 continues at 950 where electrical connectors 250 conductively coupled to the x-ray imager and sensor(s) are thread through corresponding opening(s) 260. As described above, more than one electrical connector 250 may be thread through an opening 260. For example, separate openings 260 may be utilized for supplying power and transmitting data, to allow for versatility of positioning electronic components in the housing. Also, an image sensor 210 may be conductively coupled to more than one electrical connector 250. Next, at 960, a resealable circumferential gasket is fitted around each electrical connector 250, and then seated in the corresponding opening 260, thereby providing a resealable seal at the opening 260.

Following 960, method 900 continues at 970 where a resealable seal 240 is positioned at a top surface 224 of the raised flange 220, thereby moving the sealing surfaces of the x-ray detector apart from the x-ray imager (e.g., the scintillator and the image sensor) and any surfaces directly adjacent thereto. The resealable seal is formed by removably fastening the cover 230 at the sealing region 232, on the top surface 224 of the raised flange 220. As described above with reference to FIG. 4C, the cover can be removably fastened in various ways including being bolted, bracketed, riveted, screwed, and the like. At 980, after resealably sealing the x-ray detector, the housing may be purged with a dry inert gas through the pluggable port 598 to remove any moisture therein. Next, at 990, the pluggable port 598 may be removably plugged and a leak test may be performed to determine the hermeticity of the resealable seal between the cover 230 and the raised flange 220, and at each opening 260. After 990, method 900 ends.

Figure 9:
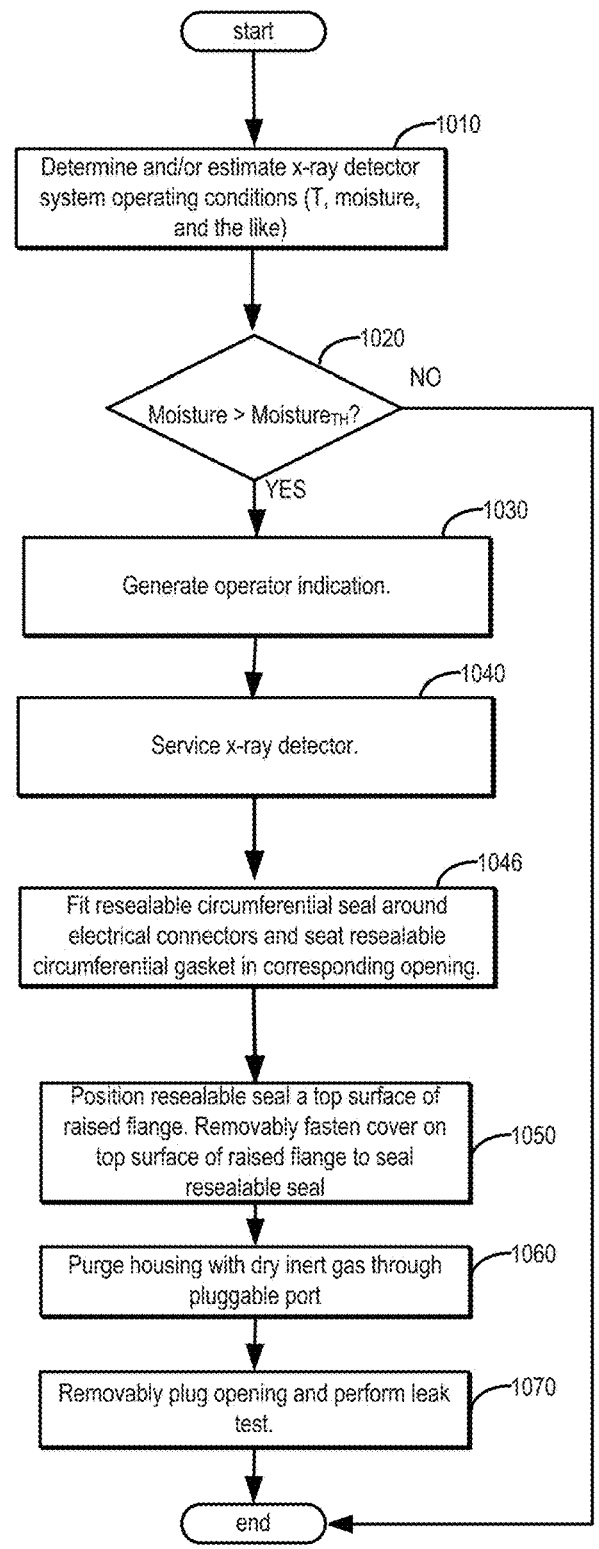
FIG. 9 is an example flow chart for a method of resealing the x-ray detectors of FIGS. 2A, 2B, 3, 4A-4C, and 7.

Turning now to FIG. 9, it illustrates an example method 1000 for resealing an x-ray detector system. Method 1000 may comprise executable instructions on board a controller that may executed by a computer processor conductively coupled (wired) to the x-ray detector. Method 1000 begins at 1010 where the x-ray detector system operating conditions such as the temperature, oxygen level, and/or moisture inside the x-ray detector housing are determined. At 1020, the controller determines if one or more of the sensed operating conditions such as temperature, oxygen level, and/or moisture have exceeded a threshold. For example, as shown in FIG. 9, method 1000 determines if the moisture is greater than a threshold moisture, $Moisture_{TH}$. If $Moisture > Moisture_{TH}$, method 1000 continues at 1030, where the controller may generate an operator indication to warn the x-ray detector operator that a sensed condition has crossed a threshold level. The operator indication may comprise an audio and/or visual alarm, for example.

At 1040, in response to the operator indication at 1030, the x-ray detector may be serviced at 1040. Servicing the x-ray detector may comprise opening one or more of the resealable seal between the cover 230 and the raised flange 220, and at the one or more openings 260. After unsealing the x-ray detector, the x-ray imager and other components positioned inside the housing may be inspected, repaired, and/or replaced. For example, a faulty moisture sensor may be replaced, additional getter material may added to an interior surface of the housing, a resealable seal 240 may be replaced, a resealable circumferential seal 256 may be replaced, an electrical connector 250 may be replaced, and the like. After servicing the detector at 1040 method 1000 continues at 1046 and 1050 where the resealable circumferential seals may be fit around the electrical connectors and reseated in the openings, and x-ray detector may be resealed by positioning the resealable seal 240 at the top surface 224 of the raised flange 220 and removably fastening the cover on the top surface of the raised flange, respectively. Similar to steps 980 and 990 of method 900, after resealably sealing the x-ray detector at 1046 and 1050, method 1000 may continue at steps 1060 and 1070 where the housing is purged with a dry inert gas and leak testing is performed. After 1070 and at 1020 when $Moisture < Moisture_{TH}$ method 1000 ends.

As provided above, scintillator sealing for solid state x-ray detectors is shown and described. In one embodiment, an x-ray detector is provided including a housing, including a cover removably fastened on a flange of a flanged base and forming a seal therebetween, the flanged base including a bottom surface and the flange surrounding a perimeter of the bottom surface and an x-ray imager positioned on the bottom surface, the x-ray imager including a scintillator and an image sensor. The, seal may semi-hermetically enclose the x-ray imager in the housing, and may be positioned nonadjacently to surfaces in contact with the x-ray imager. In some examples, in the absence of the seal between the cover and the flanged base, the semi-hermeticity of the x-ray imager may be lost. Moreover, in some examples, the cover may include a thicker sealing region that contacts the flange and encloses a thinner central region, the thinner central region comprising an x-ray transmissive material.

Further, in some examples, a semi-hermetically resealable material sandwiched between the cover and the flange and surrounding the perimeter the bottom surface may be provided. The semi-hermetically resealable material may include a compressible gasket. Further, a getter material may be positioned at an interior surface of the housing. The getter material may be a coating, in some examples.

An x-ray imaging system is also provided including a power source, a housing, including a cover removably fastened on a raised flange of a flanged base thereby forming a resealable seal therebetween, an x-ray imager, including a scintillator and an image sensor, the x-ray imager positioned on a bottom surface of the flanged base inside the housing below and nonadjacent to the resealable seal, the raised flange surrounding a perimeter of the bottom surface, and an electrical connector conductively coupled to the x-ray imager and the power source. The x-ray imaging system may include an electrical connector conductively coupled to the x-ray imager, the electrical connector capable of transmitting signals output from the x-ray imager externally from the housing.

In some examples, the resealable seal may be a resealable hermetic seal. In additional examples, an opening in the raised flange may be provided through which the electrical connector is sealably threaded. Further, the electrical connector may be a resealable circumferential seal surrounding a transverse cross section of the electrical connector, wherein a cross-section of the resealable circumferential seal corresponds to a cross-section of the opening, and seating the resealable circumferential seal in the opening seals the opening thereby allowing the electrical connector to be sealably threaded through the opening.

Additionally, a moisture sensor may be positioned in the housing and conductively coupled to the electrical connector. A controller external to the housing and conductively coupled to the electrical connector may be provided where the controller includes executable instructions stored thereon to, in response to a signal from the moisture sensor indicating a moisture level above a threshold moisture level, to generate an indication to repair the x-ray imager.

A method of assembling an x-ray detector including an x-ray imager, a housing, and an electrical connector conductively coupled to the x-ray imager is also provided. In one example method, the method may include positioning the x-ray imager on a bottom surface of the housing, the housing comprising a cover and a raised flange surrounding a perimeter of the bottom surface, and the x-ray imager comprising a scintillator and an image sensor; and sealing the x-ray imager within the housing, including removably affixing the cover on a top surface of the raised flange to form a resealable seal between the cover and the raised flange, wherein the resealable seal is positioned outside of a path of x-rays incident at the x-ray imager.

The method may include sandwiching a reusable sealing material between the cover and the raised flange. Further, the method may include, purging the housing with a moistureless purge gas through an opening in the housing, and sealing the opening after purging the housing. In some example, the method may include placing getter material at an interior surface of the housing.

The method also may include threading the electrical connector through a resealable opening in the housing, where the electrical connector includes a compressible gasket surrounding a transverse cross-section of the electrical connector. The method further may include sealing the resealable opening by hermetically seating the compressible gasket in the resealable opening.

In this way, the technical effect of providing a seal for a digital x-ray panel in a simple, low cost way can be achieved. Further technical effects are listed as follows. In the case where the seal is reusable and resealable, the technical effect of facilitating repair and refurbishment of the device is provided. Further still, the seal is positioned away from the detector-active region and thus does not interfere with the detector operation, and reduces a risk of damaging the detector components during manufacturing. Further still, positioning the seal away from the detector-active region can facilitate addition of other components within the x-ray detector housing such as getter material, sensors, electrical connectors, and the like, which can increase the performance and functionality of the x-ray detector. Further still, the seal facilitates sealing multiply-tiled large image array detectors within a single x-ray detector. Further still, the resealable seal may comprise a semi-hermetic resealable seal or a hermetic resealable seal.

It is to be understood that the description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to those of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

Additionally, the term pixel is used throughout the specification and should be interpreted to include one or more pixel. The term pixel is not restricted by any number because of the use of singular or multiple form.

This written description uses examples to disclose several embodiments of the inventive subject matter and also to enable any person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

The invention claimed is:

1. An x-ray detector, comprising:
a housing, including a cover removably fastened on a flange of a flanged base and forming a seal therebetween, the flanged base including a bottom surface and the flange surrounding a perimeter of the bottom surface;
an x-ray imager positioned on the bottom surface, the x-ray imager including a scintillator and an image sensor; and
a moisture sensor positioned in the housing,
wherein the seal semi-hermetically encloses the x-ray imager in the housing, and is positioned nonadjacently to surfaces in contact with the x-ray imager.

2. The x-ray detector of claim 1, wherein in absence of the seal between the cover and the flanged base, semi-hermeticity of the x-ray imager is lost.

3. The x-ray detector of claim 2, further comprising a semi-hermetically resealable material sandwiched between the cover and the flange and surrounding the perimeter the bottom surface.

4. The x-ray detector of claim 3, wherein the semi-hermetically resealable material comprises a compressible gasket.

5. The x-ray detector of claim 4, wherein the cover comprises a thicker sealing region that contacts the flange and encloses a thinner central region, the thinner central region comprising an x-ray transmissive material.

6. The x-ray detector of claim 5, further comprising getter material positioned at an interior surface of the housing.

7. The x-ray detector of claim 6, wherein the getter material comprises a coating.

8. An x-ray imaging system, comprising:
a power source;
a housing, including a cover removably fastened on a raised flange of a flanged base thereby forming a resealable seal therebetween; and
an x-ray imager, including a scintillator and an image sensor, the x-ray imager positioned on a bottom surface of the flanged base inside the housing below and nonadjacent to the resealable seal, the raised flange surrounding a perimeter of the bottom surface;
an electrical connector conductively coupled to the x-ray imager and the power source; and a moisture sensor positioned in the housing and conductively coupled to the electrical connector.

9. The x-ray imaging system of claim 8, wherein the electrical connector is configured to transmit signals output from the x-ray imager externally from the housing.

10. The x-ray imaging system of claim 8, wherein the resealable seal comprises a resealable hermetic seal.

11. The x-ray imaging system of claim 8, further comprising an opening in the raised flange through which the electrical connector is sealably threaded.

12. The x-ray imaging system of claim 8, wherein: the electrical connector comprises a resealable circumferential seal surrounding a transverse cross section of the electrical connector, a cross-section of the resealable circumferential seal corresponds to a cross-section of the opening, and seating the resealable circumferential seal in the opening seals the opening to allow the electrical connector to be sealably threaded through the opening.

13. The x-ray imaging system of claim 8, further comprising a controller external to the housing and conductively coupled to the electrical connector, the controller including executable instructions stored thereon to, in response to a signal from the moisture sensor indicating a moisture level above a threshold moisture level, generate an indication to repair the x-ray imager.

14. A method of assembling an x-ray detector including an x-ray imager, a housing, and an electrical connector conductively coupled to the x-ray imager, comprising:
positioning the x-ray imager on a bottom surface of the housing, the housing comprising a cover and a raised flange surrounding a perimeter of the bottom surface, and the x-ray imager comprising a scintillator and an image sensor;
providing a moisture sensor positioned in the housing and conductively coupled to the electrical connector; and
sealing the x-ray imager within the housing, including removably affixing the cover on a top surface of the raised flange to form a resealable seal between the cover and the raised flange, wherein the resealable seal is positioned outside of a path of x-rays incident at the x-ray imager.

15. The method of claim 14, wherein sealing the x-ray imager further comprises sandwiching a reusable sealing material between the cover and the raised flange.

16. The method of claim 15, further comprising purging the housing with a moistureless purge gas through an opening in the housing, and sealing the opening after purging the housing.

17. The method of claim 16, further comprising placing getter material at an interior surface of the housing.

18. The method of claim 17, further comprising threading the electrical connector through a resealable opening in the housing, the electrical connector comprising a compressible gasket surrounding a transverse cross-section of the electrical connector.

19. The method of claim 18, further comprising sealing the resealable opening by hermetically seating the compressible gasket in the resealable opening.

* * * * *